(12) United States Patent
Raz et al.

(10) Patent No.: US 6,181,414 B1
(45) Date of Patent: Jan. 30, 2001

(54) INFRARED SPECTROSCOPY FOR MEDICAL IMAGING

(75) Inventors: Ryan S. Raz; Gordon Rosenblatt; Daniel S. Maclean, all of Toronto (CA)

(73) Assignee: Morphometrix Technologies Inc, Toronto (CA)

( * ) Notice: Under 35 U.S.C. 154(b), the term of this patent shall be extended for 0 days.

(21) Appl. No.: 09/368,521

(22) Filed: Aug. 5, 1999

Related U.S. Application Data

(63) Continuation of application No. PCT/CA98/00092, filed on Feb. 6, 1998.

(51) Int. Cl.⁷ ........................................ G01J 3/00
(52) U.S. Cl. .................. 356/51; 250/339.05; 348/79; 348/166
(58) Field of Search ................ 356/51; 250/339.05; 348/65, 79, 166, 168

(56) References Cited

U.S. PATENT DOCUMENTS

| | | | |
|---|---|---|---|
| 3,806,257 | 4/1974 | Amos | 356/432 |
| 5,910,816 | * 6/1999 | Fontenot et al. | 348/65 |

FOREIGN PATENT DOCUMENTS 196 23 821
A1   12/1996  (DE) .

0 174 778 A1   3/1986  (EP) .

* cited by examiner

Primary Examiner—F. L. Evans
(74) Attorney, Agent, or Firm—Ridout & Maybee (57) ABSTRACT

A multi-channel spectral imaging module for an automated testing system for cytological applications. The multi-channel spetral imaging module generates four channels of digitized images of a cytological specimen for further processing in the automated testing system. The multi-spectral imaging module comprises a visible light source and an infrared light source, an optical imaging module, a prism module, and an output stage. The cytological specimen is strobed by the visible light and infrared light sources and the illuminated images of the specimen are focussed and coupled to the prism module by the optical imaging module. The prism module breaks the illuminated image into four channels comprising three visible light channels and an infrared channel. The output stage comprises a CCD array sensor for each channel. The CCD array sensor digitizes the image for channel and produces an output for further processing. The digitized output from the infrared channel provides additional information which is used by the automated testing system. The additional information derived from the infrared channel includes segmentation information, new identifying features for the specimen, and discrimination measures independent of the visible light channels. In another embodiment, a fifth channel is provided for a reference infrared output and the two infrared channels are operated in a differential mode.

12 Claims, 9 Drawing Sheets

INFRARED SPECTROSCOPY FOR MEDICAL IMAGING

This application is a continuation of our International Patent Application No. PCT/CA98/00092 filed Feb. 6, 1998.

FIELD OF THE INVENTION

The present invention relates to Near Infrared (NIR) spectroscopy and more particularly to a multi-channel spectral imaging module utilizing NIR for discriminating between normal and pre-cancerous cells prepared in the form of cells or cell groupings on a microscope slide.

BACKGROUND OF THE INVENTION

Automated systems for the rapid and accurate screening of cytological specimens are being developed to address cost, labour and liability issues. One such example is the development of automated systems for the well-known Pap (i.e. Papanicolaou) test. The Pap test is a screening test for evidence of pre-cancerous lesions in exfoliated cervical cells. The Pap test involves a tedious, manual examination of tens of thousands of cervical epithelial cells, and as a result is costly to apply and is subject to human error. Nevertheless, the Pap test has an enviable record of reducing cervical cancer mortality in the countries where it is applied. Thus, an automated alternative has been eagerly sought.

The most successful automated Pap test systems emulate cytotechnologists, the highly-trained professionals that screen this and other tests. As the cytotechnologist relies on the visual evaluation of cervical cells, so the automated systems depend upon some type of image analysis.

For machines, image analysis typically comprises a series of four steps. First, the microscopic image is digitized to the image into a form that may be readily used by the electronic hardware and the software instruction set for the machine. Second, the digitized image is segmented. Segmentation involves separating the relevant portions of the digitized image from the rest of the image. In most image analysis systems, segmentation comprises the most difficult and crucial step in the processing sequence. Since segmentation must e done well in advance of any pattern recognition operation, the segmentation procedure must be designed to use visual keys such as edges to find and separate the important image components. The third step is known as feature extraction. Each of the segmented regions or objects in the image is subjected to a range of mathematical measures that seek to encapsulate the visual appearance in numerical form. The fourth step known as classification involves using the numerical features to arrive at some type of conclusion about the object's identity.

Near Infrared (NIR) spectroscopy is an established technique for the extraction of quantitative measures in a wide variety of materials. Recently, NIR spectroscopy has been applied to human tissue samples in order to discriminate between cancerous or pre-cancerous tissue and normal tissue.

Most of the absorption spectra of organic compounds are generated by the vibrational overtones or the combination bands of the fundamentals of O—H (oxygen-Hydrogen), C—H (Carbon-Hydrogen), N—H (nitrogen-Hydrogen), and C—C (Carbon-Carbon) transitions. As these transitions fall in the mid-infrared regions, NIR spectra in the easily accessible range between 0.7 microns and 2.5 microns are produced. However, the strengths of these spectra are one to three orders of magnitude smaller than the associated fundamentals and therefore special care needs to be taken to recover and analyze this information.

Known research into the NIR response of normal and pre-cancerous human tissue has uncovered a host of structural and chemical changes which may be used to discriminate between normal and pre-cancerous tissues. These features include increases in glycogen content, extensive hydrogen bonding of phosphodiester groups in nucleic acids, tighter physical packing of nucleic acids, phosphorylation of C—OH groups in carbohydrates and proteins, increased disorder of methylene chains in membrane lipids, increased ratio of methyl to methylene, reduction in the hydrogen bond strength in the amide groups of α-helical segments and an increase in the hydrogen bond strength in the amide groups of β-sheet segments.

On the basis of these results, proposals for NIR-based cancer screening protocols have been made, including a screening protocol for the early detection of pre-cancerous lesions of the uterine cervix and carcinomatous breast tissue.

BRIEF SUMMARY OF THE INVENTION

The present invention provides a multi-channel spectral imaging module utilizing NIR spectroscopic techniques to produce a rapid and effective discrimination between normal and pre-cancerous cells prepared in the form cells or cell groupings on a microscope slide or similar sub-structure.

The subject invention is intended to function as part of an automated system comprising components described in co-pending patent applications entitled Automated Scanning of Microscope Slides International Patent Application No. CA96/00475 filed Jul. 18, 1996, Pipeline Processor for Medical and Biological Applications U.S. patent application Ser. 08/683,440 filed Jul. 18, 1996, Multi-Spectral Segmentation International Patent Application No. CA96/00477 filed Jul. 18, 1996, Neural-Network Assisted Multi-Spectral Segmentation International Patent Application No. CA96/00619 filed Sep. 18, 1996, Automated Focus System International Patent Application No. CA96/00476 filed Jul. 18, 1996, Window Texture Extraction International Patent Application No. CA96/00478 filed Jul. 18, 1996, Multi-Spectral Imaging System and Method for Cytology International Patent Application No. CA97/00318 filed May 9, 1997, and Pipeline Processor for Medical and Biological Image Analysis International Patent Application No. CA97/00878 filed Nov. 20, 1997.

In one aspect, the present invention comprises a multi-channel spectral imaging module for an automated testing system for cytological applications. According to this aspect of the invention, one or two of the channels in the imaging system comprise NIR (Near Infrared) channels. The NIR channels augment the visible spectrum images produced by a multi-spectral camera system and provide new and useful channels of information. The NIR channels are used to improve segmentation performance, to create a new set of features for classification, or as discrimination measures independent of the visible light channels. According to another aspect of the invention, restricting the use of the NIR channels to regions of the samples that contain nuclear material improves the effective signal-to-noise ratio of the measurement over bulk tissue measurements thereby improving the discrimination capability of the system. In another aspect, a pair of differential NIR channels (one channel acting as an interrogator, the other channel providing a reference) are utilized to provide a high-speed and real-time scan of cellular material to quickly discriminate between normal and abnormal cells or tissue and may be extended to other important diagnostic properties of the cells.

The NIR channels are effective for producing rapid and effective discrimination between normal and pre-cancerous cells prepared in the form cells or cell groupings on a microscope slide or similar sub-structure.

In a first aspect, the present invention provides a multi-channel spectral imaging module for an automated testing system for cytological application, said multi-channel spectral imaging module comprising: (a) a light source module for illuminating a cytological specimen, said light source including a visible light source and an infrared light source and a control input for actuating said visible and infrared light sources; (b) an optical imaging module for receiving illuminated images of said cytological specimen and including a lens system for focusing said illuminated images; (c) a prism module for receiving said illuminated images from said optical imaging module, said prism module including three prism elements for producing three respective image channels in the visible spectrum and a fourth prism element for producing an image channel in the infrared spectrum, and said prism module further including a digitizer for each of said channels for converting the image into an output signal.

In a second aspect, the present invention provides a method for generating multi-spectral image date for a cytological specimen, said method comprising the steps of: (a) exposing said cytological specimen to a burst of broad-band light; (b) separating said burst of broad-band light images into a plurality of spectral bands; (c) simultaneously capturing an image for each of said spectral bands and generating electrical signals corresponding to each of said captured spectral images; (d) converting the electrical signals corresponding to said captured spectral images into a data form suitable for further processing by an automated testing system; (e) exposing said cytological specimen to a burst of light in an infrared spectral band; (f) simultaneously capturing an image in said infrared spectral band and an generating electrical signal corresponding to said captured infrared spectral image; (g) converting the electrical signal corresponding to said captured infrared spectral image into a data form suitable for further processing by an automated testing system.

BRIEF DESCRIPTION OF THE DRAWINGS

Reference will now be made to the accompanying drawings which show, by way of example, a preferred embodiment of the present invention, and in which.

DETAILED DESCRIPTION OF THE PREFERRED EMBODIMENT

The automated system for cytological testing as described in the co-pending applications by the common owner of the present invention as outlined above utilized three narrowly defined optical bands in the visible range to characterize the cells under examination. The three bands are chosen so as to maximize the optical contrast between the nucleus and cytoplasm of the cell and the background material. Then, using linear, non-linear and neural-network assisted procedures, the information obtained from three bands is used to generate a segmentation map of the image on a pixel-by-pixel basis. The segmentation map is subjected to further processing to improve the integrity and quality of the captured information. Next, a feature extraction operation is performed. Feature extraction involves subjecting each of the segmented regions or objects in the image to a range of mathematical measures that seek to encapsulate the visual appearance in numerical form. The fourth step known as classification involves using the numerical features to arrive at some type of conclusion about the object's identity. It will be appreciated that the utilization of three channels of information provides an information foundation which ensures the quality and reliability of the captured information during the various processing steps performed by the automated system.

As will now be described, the present invention comprises a multi-channel spectral imaging module for the multi-spectral camera system described in the co-pending patent application entitled Multi-Spectral Imaging System and Method for Cytology International Patent Application No. CA97/00318 filed May 9, 1997 by the common owner of the subject invention. The multi-spectral camera as described in the co-pending application comprises an electro-optical system that creates digitized, spectrally-separated images for computer acquisition, display and analysis. The system operates with high resolution and at high speed, simultaneously producing three, spectrally-resolved, spatially coincident micro-graphic images for capture and storage by computer. The simultaneous acquisition of spectrally-resolved images in the visible light region permits the high-speed application of polychromatic stain protocols in automated analysis procedures. The simultaneous capture of the images also ensures that image registration is maintained for image processing operations which as will be appreciated is a problem in systems which serially capture images.

Figure 9:
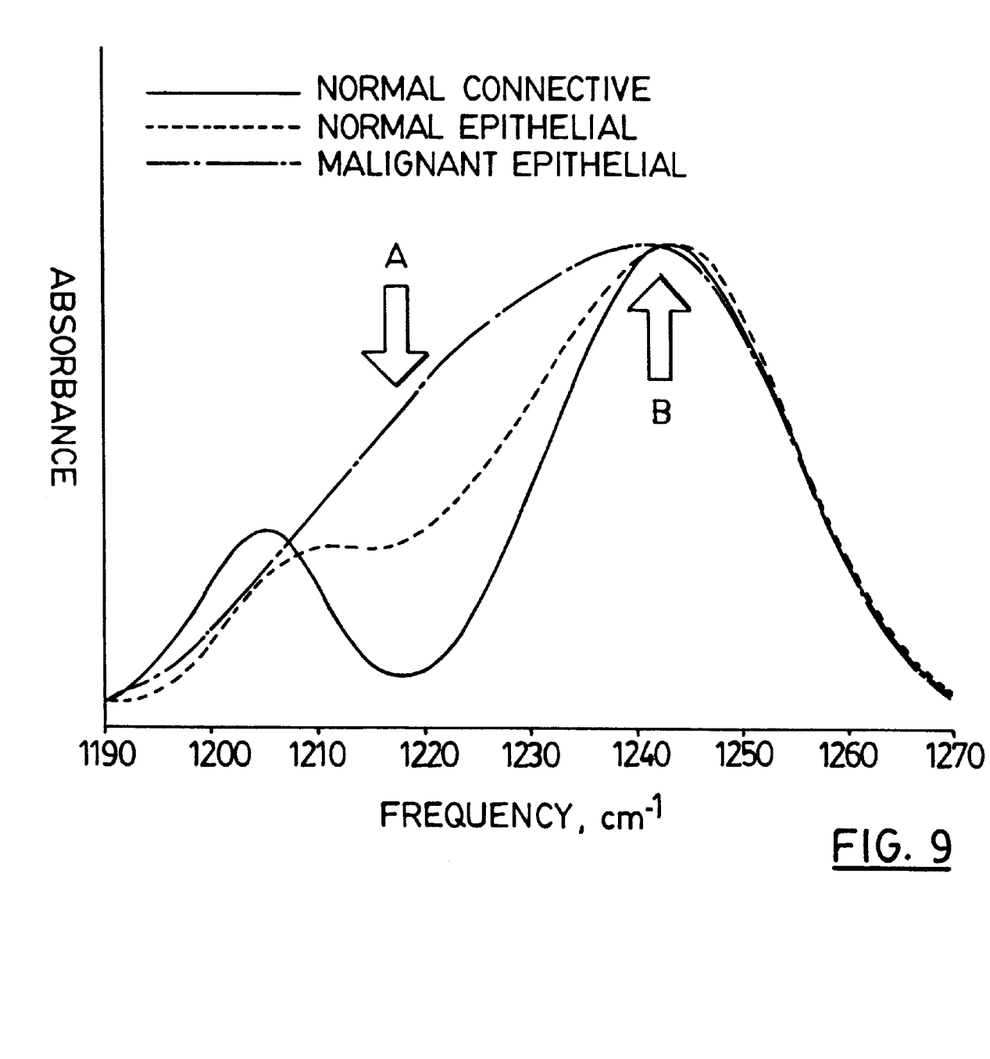
FIG. 9 shows the known Infrared spectra of cervical tissues in the asymmetric phosphate stretching region.

The multi-channel spectral imaging module according to the present invention comprises one or two NIR (Near Infrared) channels. The NIR channels are utilized to augment the visible spectrum images produced as per the common applicant's multi-spectral camera system to provide a new and useful channel of information. The near-infrared absorption properties of the cervical epithelial cells may be integrated into this technique to yield a new channel of information. As shown in FIG. 9, normal epithelial nuclei reach an absorption plateau in the range of 1215 $cm^{-1}$ while malignant epithelial nuclei near an absorption peak according to known studies (ex., PTT Wong, et al. Applied Spectroscopy 48(7) 1058 (1993)). The ratio of absorbencies, measured on bulk material, is approximately 1.8 in a 5 $cm^{-1}$ range centred at this frequency. Nearby, as shown in FIG. 9, the absorbencies of the normal and malignant materials converge at 1240 $cm^{-1}$, providing a suitable channel for response normalization. These narrow NIR bands are ideally exploited for discriminative purposes in the context of present invention.

As will be described in further detail below, the NIR channels are used to improve segmentation performance, to create a new set of features for classification, or as discrimination measures on their own. According to another aspect, restricting the use of the NIR channels to regions of the samples that contain nuclear material also improves the effective signal-to-noise ratio of the measurement over bulk tissue measurements thereby improving the discrimination capability of the system. In another aspect, a pair of differential NIR channels (i.e. the 1215 $cm^{-1}$ band providing an interrogation channel and the 1240 $cm^{-1}$ band providing a reference channel) are utilized to provide a high-speed and real-time scan of cellular material to quickly discriminate between normal and abnormal cells or tissue and this embodiment may be extended to other important diagnostic properties of the cells.

Figure 1:
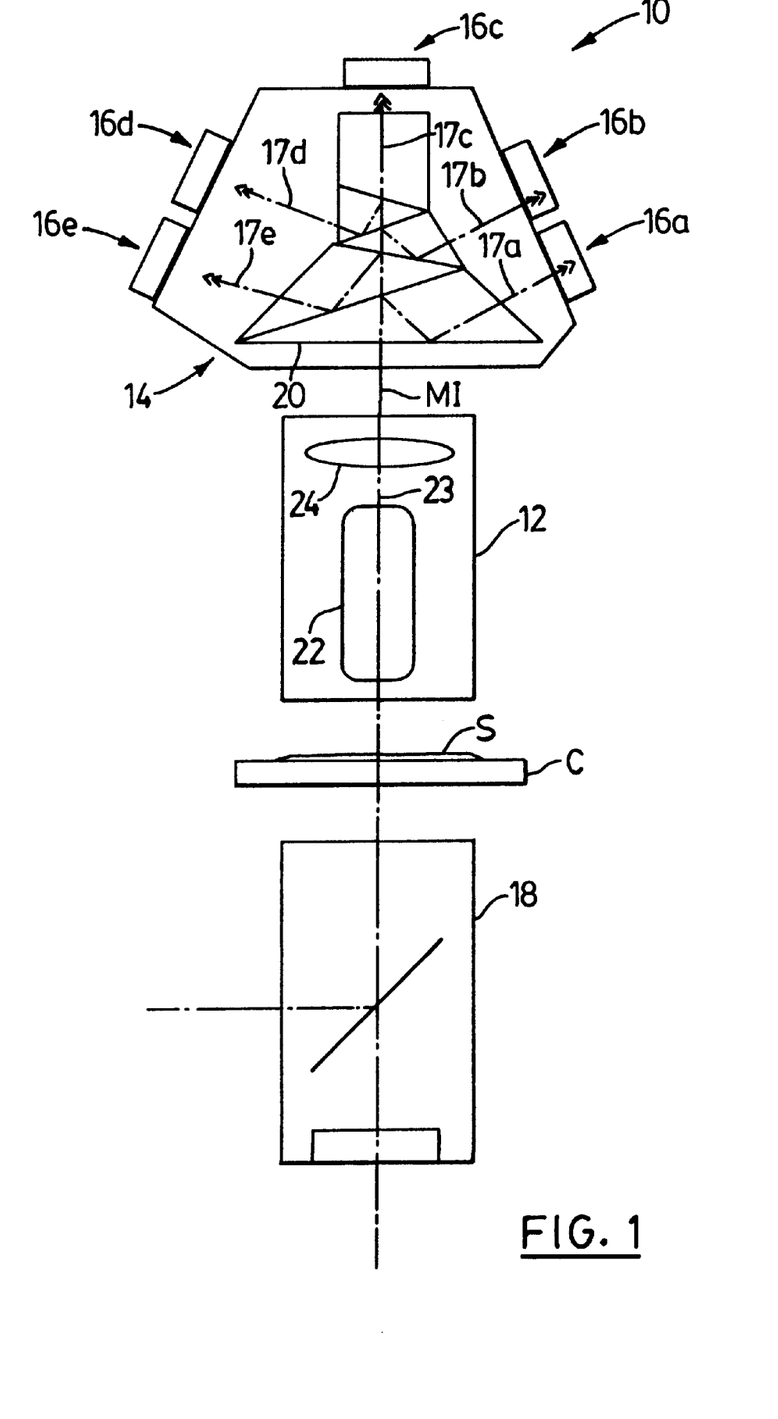
FIG. 1 shows in diagrammatic form a multi-channel spectral imaging module according to the present invention.

Reference is made to FIG. 1 which shows a five-channel multi-spectral imaging module 10 according to the present invention. The multi-spectral imaging module 10 comprises an optical imaging module 12, a prism module 14, a series of CCD (Charge Coupled Device) array sensors 16, and an illumination mixer 18.

The principal function of the optical imaging module 12 is gathering a microscope image of a specimen S (e.g. a cytological specimen S placed on a suitable carrier such as a slide C) and enlarging the microscopic image with minimal monochromatic or chromatic aberrations. As shown in FIG. 1, the optical imaging module 12 comprises two lens systems: an objective lens 22 and a telan lens 24. The objective lens 22 is designed for infinite-conjugate operation meaning that the object is placed in the focal plane of the objective lens 22 and a real image is produced at an infinite distance away on the optical axis 23. The objective lens 22 alone carries all of the monochromatic and chromatic error corrections and produces a flat-image field over the area of interest. The telan lens 24 is used to gather this infinite-conjugate image from the objective lens 22 and reconstruct a real magnified image MI a short distance from the optical imaging module 12. The magnified image MI is optically coupled to the prism module 14. The magnifying power of optical imaging module 12 is expressed as the negative of the ratio of the two effective focal lengths of the objective 22 and telan 24 lenses, as follows:

$$\text{Magnification} = -f_{TELAN}/f_{OBJECTIVE}$$

The advantage of such an arrangement is that the magnification is independent of tube length unlike the older 160 mm DIN standard for microscopes as will be familiar to those skilled in the art.

The prism module 14 is optically coupled to the output of the optical imaging module 12 to receive the magnified image MI. The prism module 14 comprises an optical prism assembly 20 which is used to create five-spectrally resolved channels 17a to 17e. the channels 17 for the imaging system comprise three visible-light channels 17a, 17b and 17c, and single NIR channel 17d or a differential NIR channel pair 17d and 17e. The visible-light channels 17a, 17b, 17c comprise narrow band channels having centre wavelengths 530 nm, 577 nm and 639 nm as described in co-pending International Patent application No. CA97/00318 filed May 9, 1997.

Figure 2:
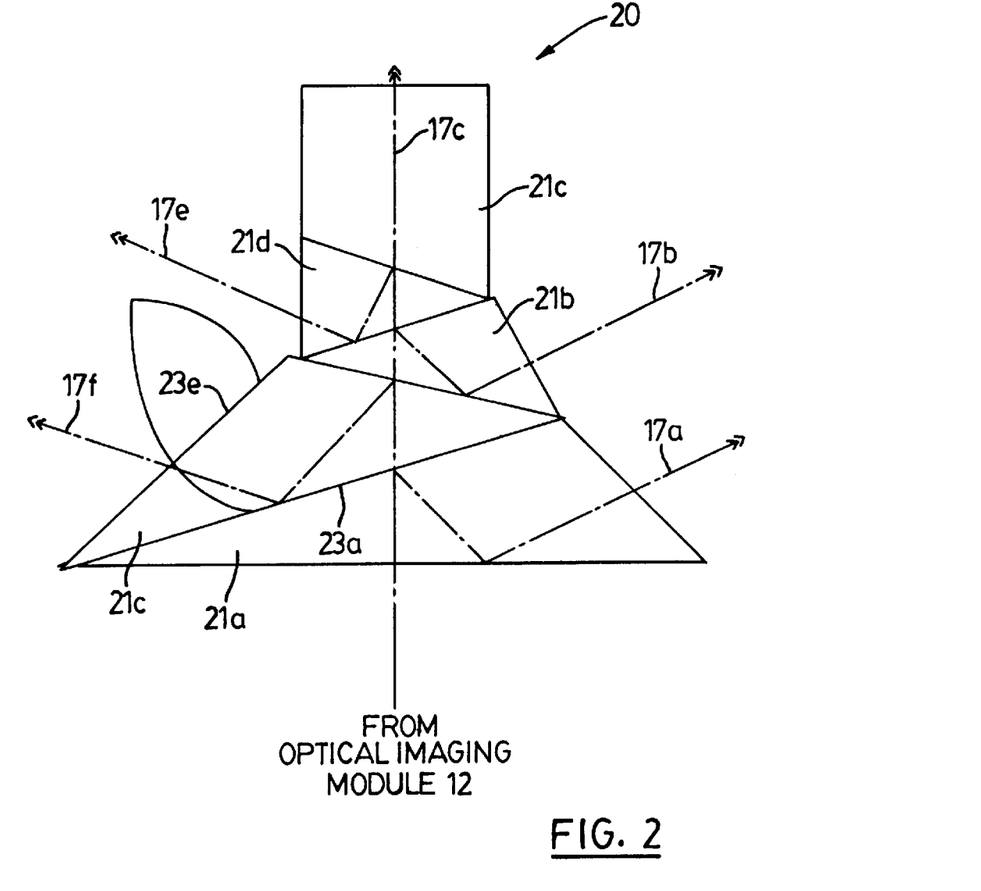
FIG. 2 shows the prism assembly of FIG. 1 in more detail.

As shown in FIG. 2, the prism assembly 20 comprises a set of five interlocking glass prisms 21, with each prism 21a, 21b, 21c, 21d, 21e, 21f corresponding to a respective channel 17a, 17b, 17c, 17d, 17e and 17f. Each glass prism 21 includes a dichroic, multi-layer interference band-pass optical filter 23 on one of its surfaces. When assembled and aligned, the prism assembly 20 receives the magnified image MI projected from the telan lens 24 in the optical imaging module 12 and creates a set of five equivalent images that have been filtered to reject all but the five bands of the respective channels 17. The prism assembly 20 re-directs each one of the five images to the associated CCD array sensor 16a along five separate paths (i.e. channels 17) to accomplish a low-loss spatial separation. Advantageously, the prism assembly 20 provides simultaneous spectral and spatial separation of the magnified image MI from the optical module 12 with high through-pout, low optical energy loss, minimal distortion and minimal mis-registration difficulties.

The CCD sensor arrays 16 are coupled to the prism module 14 and arranged to collect and digitize the spectrally-resolved images projected from the associated prism element 21 for each channel 17. The CCD sensor arrays 16 comprise charge coupled devices and are shown individually as 16a, 16b, 16c, 16d, and 16e in FIG. 1. A sensor array 16 is provided for each channel 17. The CCD sensor arrays 16 operate in parallel to simultaneously digitize the respective images from the five channels 17a to 17e. The digitized images are than transferred over a set of fibre optical links (not shown) to the subsequent stages of the automated testing system (not shown) for further processing as described in the co-pending patent applications outlined.

Figure 3:
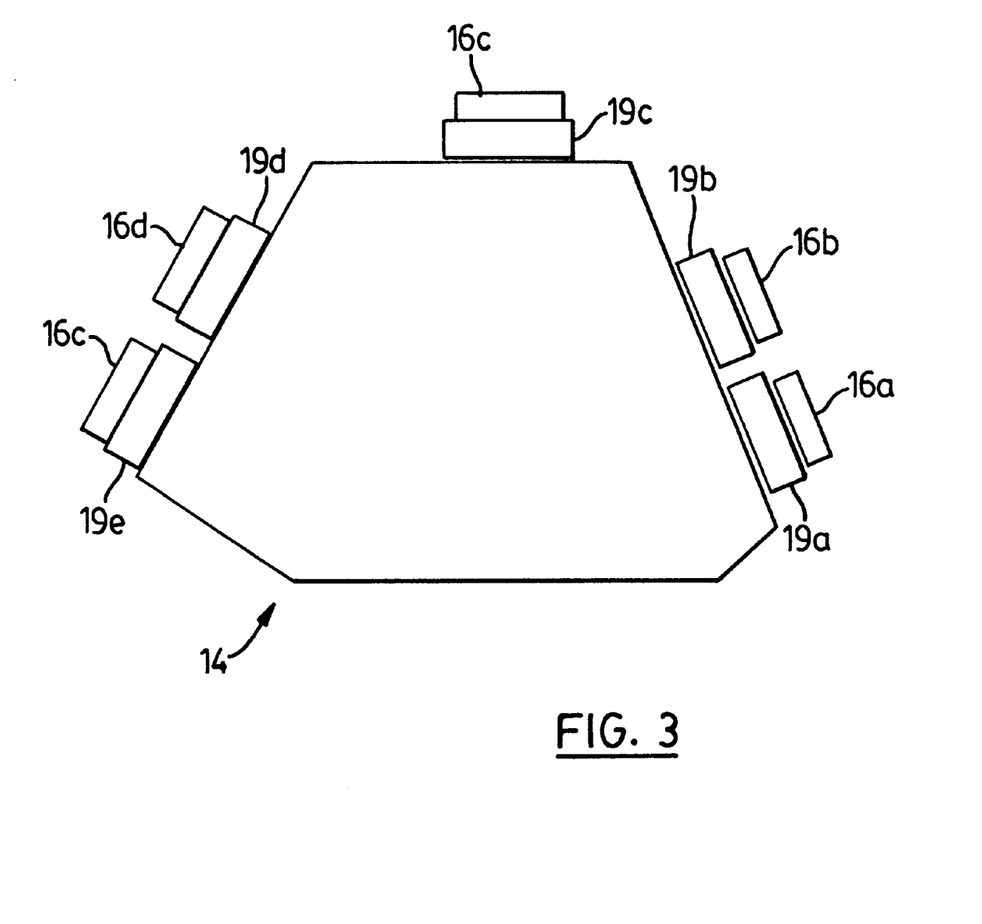
FIG. 3 shows the arrangement of CCD arrays for the imaging module of FIG. 1.

As shown in FIG. 3, each CCD sensor array 16 is mounted on a respective micro-positioning device 19, shown individually as 19a, 19b, 19c, 19c and 19e. During the initial assembly and calibration of the multi-spectral camera system (not shown) the micro-positioning devices 19 are used to align the CCD sensor arrays 16 and bring the images form each respective channel 17 into registration with the associated CCD 16. Once the initial calibration is completed and the CCD arrays 16 are registered with the image paths, it is usually not necessary to adjust the alignment again.

Figure 4:
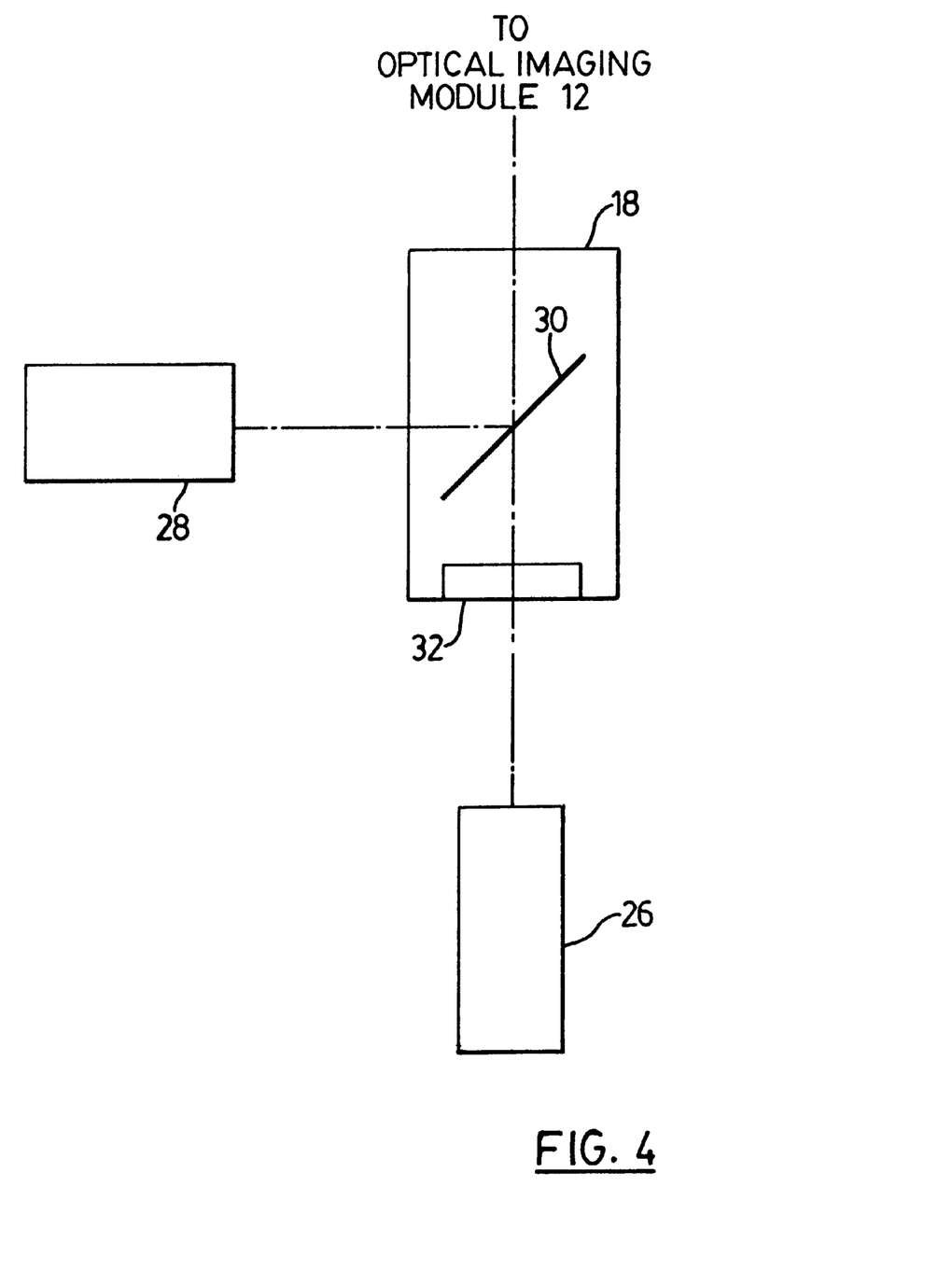
FIG. 4 shows the illumination mixer of FIG. 1 in more detail.

In order to measure the NIR absorption of the cells in the specimen S, an infrared light source 26 is provided in addition to a visible light source 28. As described in co-pending International Patent Application No. CA97/00318 filed May 9, 1997, the visible light source 28 comprises a stroboscopic flash lamp which provides the light source for the three visible optical channels 17a to 17c. The infrared light source 26 may comprise a suitable commercially available infrared lamp or a tunable laser system. The illumination mixer 18 combines the output from the visible light source 28 with the output from the infrared radiation soruce 26. As shown in FIG. 4, the illumination mixer 18 comprises a beam-splitter 30 and a shutter 32. The beam-splitter 30 is arranged to mix the outputs from the two radiation sources 26 and 28 in order to provide optimal illumination of the specimen S. The shutter 32 is used to selectively couple the output from the infrared light source 26 to the optical imaging module 12. The actuation of the shutter 32 is synchronized with the strobing of the lamp 28.

In the context of the automating testing system for cytology, the information generated from the NIR channel(s) 17d and 17e is exploited in three ways: (1) to improve segmentation performance; (2) to provide a new set of features for classification or (3) to provide an independent discrimination measure.

As described in International Patent application No. CA96/00477, the multi-spectral segmentation procedure comprises a hardware-encoded analysis routine embedded in the FPGA logic of a special-purpose computer. In order to produce a reliable segmentation output, several processing steps are applied to the images. As described, images from each of the three visible light channels (i.e. 17a, 17b, 17c) are used to create a set of absorption maps. The absorption maps show the properties of each of imaged pixels independently of material thickness. With the addition of the two NIR channels 17d and 17e, a new fourth absorption map and a new fifth absorption map are produced to show the material properties associated with the NIR formed images of the specimen S.

Figure 5:
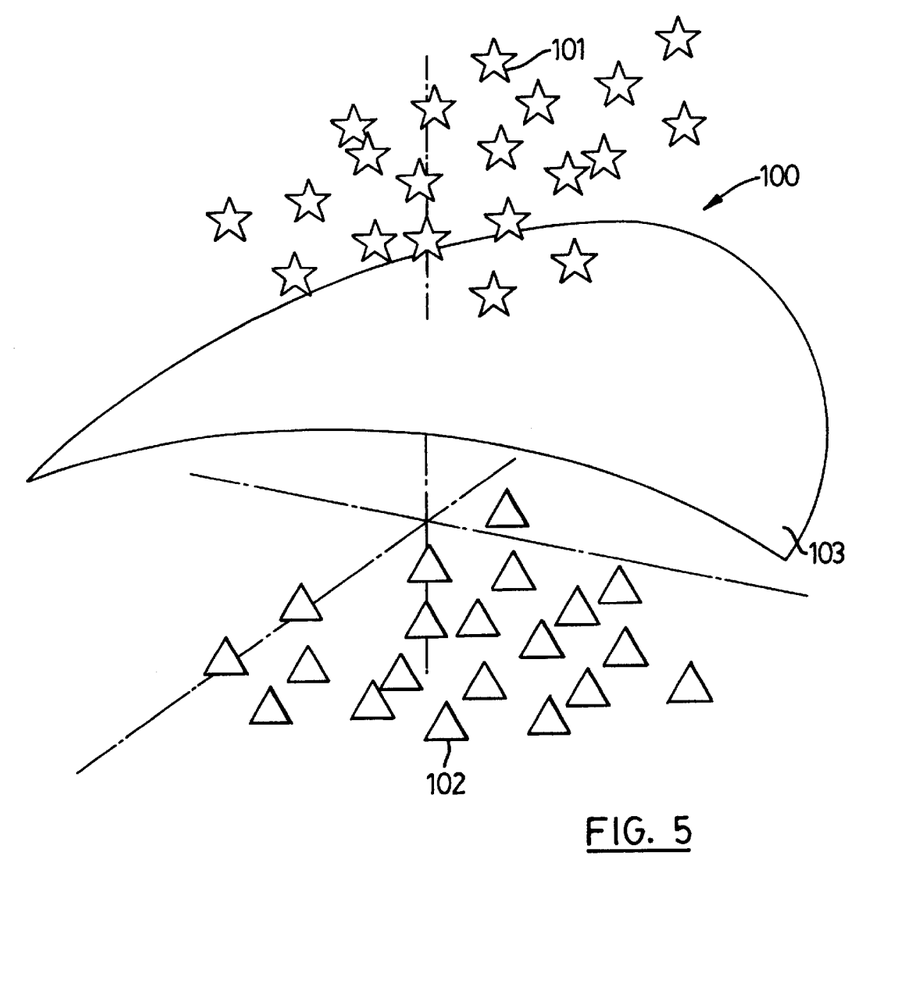
FIG. 5 depicts linear discriminant analysis utilizing outputs from the multi-channel spectral imaging module according to the present invention.

Therefore for the purposes of segmentation, the NIR channels 17d and 17e add two new axes of information to a multi-dimensional space representing the material properties of the specimen S. If enough examples of nuclei and cytoplasm are studied, this multi-dimensional space will yield discrimination information expressed in terms of the occupation of different regions of this multi-dimensional space. Thus, for every new pixel that enters the system for analysis, a point in this space can be defined and, based on the region that it occupies, its identity may be determined. This is illustrated by FIG. 5 which depicts the application of linear discriminant analysis techniques to a feature space 100 having three dimensions. The feature space 100 comprises upper 101 and lower 102 portions which are separated by a discrimination boundary 103. The upper region 101 is associated with class I while the lower portion 102 is associated with class II.

Advantageously, a segmentation technique that employs a hardware-embedded linear discriminant analysis reduces the degree of error typically associated with segmentation decisions by correlating a series of observations concerning the distribution pattern of material absorption. By hardware-encoding such a technique the process is allowed to operate at maximum speed while making a complex decision. Secondly, this technique opens the door to a multiplicity of similar types of discriminant analysis. As experimental data is further tabulated and evaluated more complex discriminant hyper-surfaces can be defined to improve segmentation accuracy. Thus, this type of algorithm can undergo a continual improvement by the adjustment of a table of coefficients that describe the decision hyper-surface without the necessity of altering the system architecture.

According to another aspect of the present invention, the two NIR channels 17d and 17e are used to provide new sets of features for the specimen S. For instance, the mathematical transformations applied to the outputs from the three visible channels 17a to 17c may be applied with equal utility to the outputs from the NIR channels 17d and 17e. Accordingly, morphological, textural, densitometric, and contextual features may be extracted from the NIR channel (s) 17d and 17e. Furthermore, a number of correlating features may be generated through comparisons with the three visible light channels 17a, 17b or 17c and the NIR channels 17d, 17e.

Figure 6:
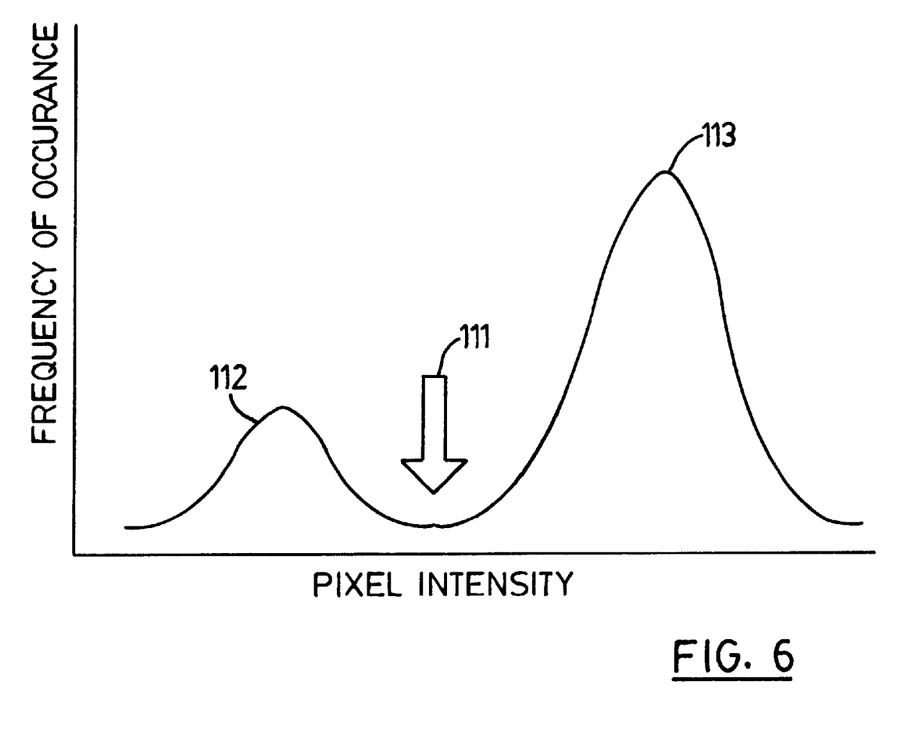
FIG. 6 shows threshold identification based on outputs from the multi-channel spectral imaging module according to the present invention.

The outputs from the NIR channels 17d and 17e are also utilized to provide an independent discrimination measure as depicted in FIG. 6. For instance after absorption baselines are calculated, the automated testing system uses a threshold 111 to determine whether any of the resultant segmented objects generated from in specimen S is abnormal 112, whereas normal objects take the distribution denoted by 113. The discrimination measures from the NIR channels 17c, 17e can form the basis of an automated decision process or may be included in a computer-aided review of the sample for full diagnosis by a cytotechnologist.

Figure 7:
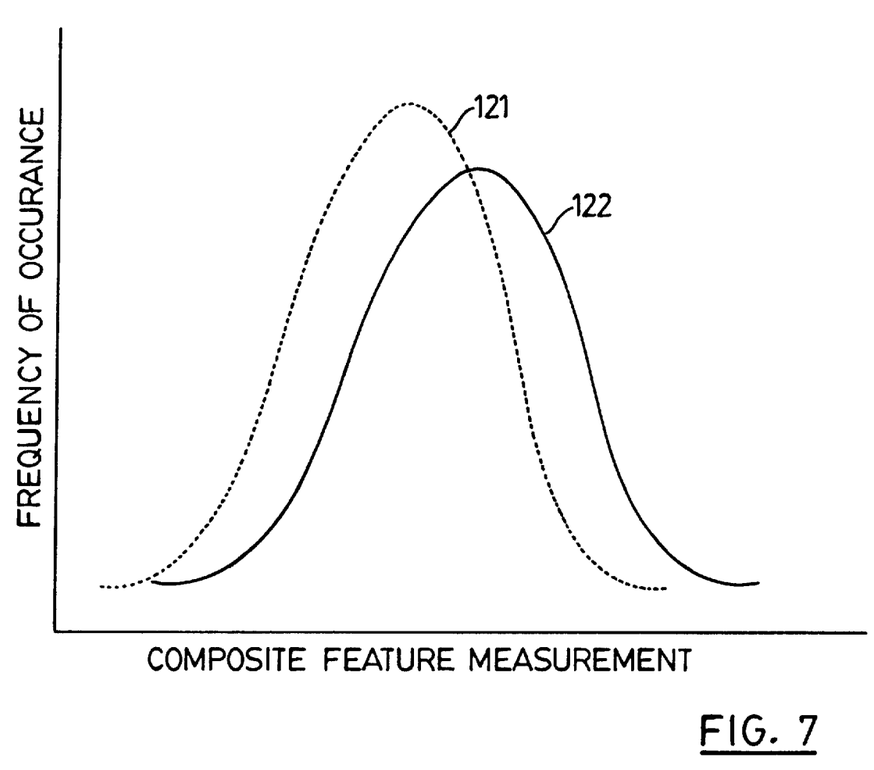
FIG. 7 shows composite feature measurement based on the outputs from the multi-channel spectral imaging module according to the present invention.

Another application of information generated from the NIR channels 17d, 17e is as part of a wide set of statistical measures for the specimen S as a whole. For example, in the case of pre-cursors to cervical cancer it is thought that the presence of a lesion will affect the physiology of neighbouring epithelial cells in some subtle manner. These subtle effects may not be apparent on a cell-by-cell basis, however, there may be a significant indication of the presence of lesion if the statistical distribution of these effects is studied. The sensitivity of the NIR absorbencies to nuclear material makes them ideal candidates for such a measure or measures. By examining the NIR response of the entire set of intermediate cervical epithelial cells, ,for example, the shape, position and weighting of the statistical distribution may indicate as shown in FIG. 7 the presence of a lesion of the uterine cervix. In FIG. 7, a normal NIR feature representation is indicated by the distribution at 121, and an abnormal NIR feature representation is indicated by the distribution at 122. Thus, the diagnosis of a pre-cancerous lesion could be performed without actually locating abnormal cells in the specimen. This would then eliminate some of the errors in screening due to poor sampling techniques.

Figure 8:
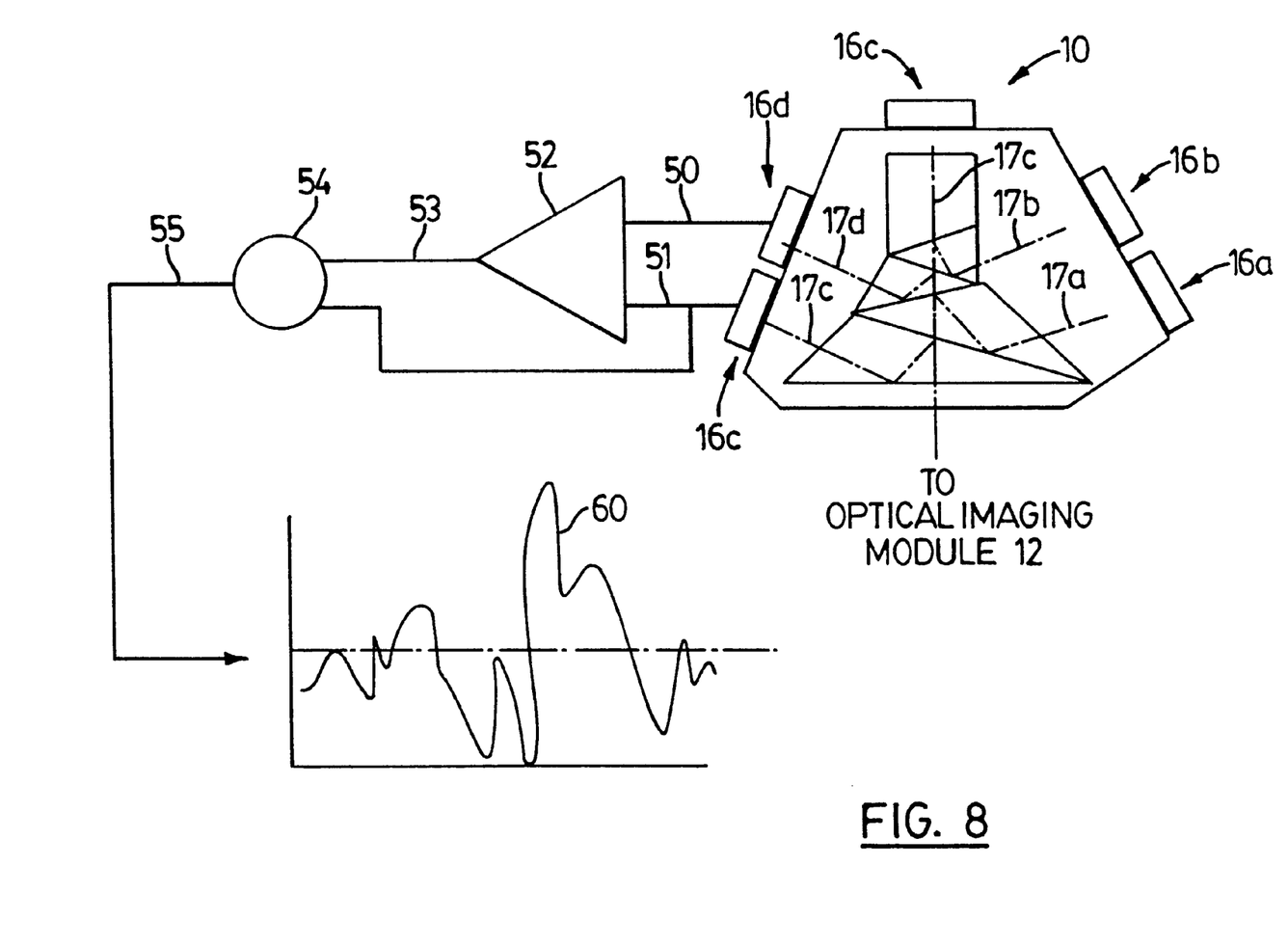
FIG. 8 an embodiment of the multi-channel spectral imaging module according to the present invention in which the NIR channels are operated in a differential mode.

According to another aspect of the present invention, the two NIR channels 17d and 17e are operated in a differential mode to provide a real-time discrimination between normal and abnormal cellular material in the specimen S (or between any two biological states that exhibit differences in this or any other pair of NIR bands). As shown in FIG. 8, the first NIR channel 17d provides an interrogation signal channel 50 and the second NIR channel 17e provides a reference signal channel 51. The interrogation 50 and reference 51 channels form the inputs for a differential amplifier 52. The differential amplifier 52 produces an output 53 based on the difference between the interrogation 50 and the reference 51 signals. The output 53 from the differential amplifier 52 provides one input for a division amplifier 54. The other input of the division amplifier 54 is coupled to the reference channel 51. The division amplifier 54 produces a pixel signal denoted by 60 at the output 55.

In operation, local variations in the thickness of the specimen S and/or variations in the illumination intensity are compensated-for by the reference channel 51. The interrogation signal 50 is subtracted from the reference signal 51 and the resulting signal 53 is normalized with the reference signal 51 by the division amplifier 54. By performing real-time monitoring of the following simple calculation:

$$\frac{I_{reference} - I_{interrogation}}{I_{reference}}$$

together with the application of a simple threshold procedure, a fast and effective discrimination is possible between two target material types. The results of the high-speed scan can then be subjected to a more detailed analysis by a computing system, and images of the suspicious material could be displayed to a human review on a monitor or the regions found could be flagged for further study by conventional means.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A multi-channel spectral imaging module for an automated testing system for cytological application, said multi-channel spectral imaging module comprising:
   (a) a light source module for illuminating a cytological specimen, said light source including a visible light source and an infrared light source and a control input for actuating said visible and infrared light sources;
   (b) an optical imaging module for receiving illuminated images of said cytological specimen and including a lens system for focussing said illuminated images;
   (c) a prism module for receiving said illuminated images from said optical imaging module, said prism module including three prism elements for producing three respective image channels in the visible spectrum and a fourth prism element for producing an image channel in the infrared spectrum, and said prism module further including a charge coupled device for each of said channels for converting the respective image into an electrical signal.

2. The multi-channel spectral imaging module as claimed in claim 1, wherein said prism module includes means for producing a second infrared output channel, said first and second infrared output channels providing a differential channel pair wherein said first infrared channel comprises an interrogation signal and said second infrared channel comprises a reference signal.

3. The multi-spectral imaging module as claimed in claim 1, wherein said image channels in the visible spectrum comprise a first optical band centered at 530 nanometers, a second optical band centered at 630 nanometers, and a third optical band centered at 577 nanometers, and said infrared spectral band comprises a 1215 $cm^{-1}$ band.

4. The multi-channel spectral imaging module as claimed in claim 2, wherein said interrogation signal comprises a 1215 $cm^{-1}$ band and said reference band comprises a 1240 $cm^{-1}$ band.

5. The multi-channel spectral imaging module as claimed in claim 1, wherein said prism module includes means for producing a second infrared output channel, said first and second infrared output channels providing information pertaining to features associated with said cytological specimen.

6. The multi-channel spectral imaging module as claimed in claim 5, wherein said information corresponds to an independent discriminate measure for said cytological specimen.

7. The multi-channel spectral imaging module as claimed in claim 5, wherein said information provides a statistical measurement associated with nuclear regions in said cytological specimen.

8. A method for generating multi-spectral image data for a cytological specimen, said method comprising the steps of:
   (a) exposing said cytological specimen to a burst of broad-band light to produce a broad-band light image;
   (b) separating said broad-band light image into a plurality of spectral bands;
   (c) simultaneously capturing an image for each of said spectral bands and generating electrical signals corresponding to each of said captured spectral images;
   (d) converting the electrical signals corresponding to said captured spectral images into a data form suitable for further processing by an automated testing system;
   (e) exposing said cytological specimen to a burst of light in an infrared spectral band;
   (f) simultaneously capturing an image in said infrared spectral band and generating an electrical signal corresponding to said captured infrared spectral image;
   (g) converting the electrical signal corresponding to said captured infrared spectral image into a data form suitable for further processing by an automated testing system.

9. A method for generating multi-spectral image data for a cytological specimen, said method comprising the steps of:
   (a) exposing said cytological specimen to a burst of broad-band light to produce a broad-band light image;
   (b) separating said broad-band light image into a plurality of spectral bands;
   (c) simultaneously capturing an image for each of said spectral bands and generating electrical signals corresponding to each of said captured spectral images;
   (d) converting the electrical signals corresponding to said captured spectral images into a data form suitable for further processing by an automated testing system;
   (e) exposing said cytological specimen to a burst of infrared light to produce an infrared light image;
   (f) separating said infrared light image into a plurality of infrared spectral bands;
   (g) simultaneously capturing an image for each of said infrared spectral bands and generating electrical signals corresponding to each of said captured infrared spectral images;
   (h) converting the electrical signals corresponding to said captured infrared spectral images into a data form suitable for further processing by an automated testing system.

10. The method for generating multi-spectral image data for a cytological specimen as claimed in claim 9, wherein said infrared spectral bands comprise a first infrared spectral band and a second infrared spectral band, said first and second infrared spectral bands providing a differential channel wherein said first infrared spectral band provides an interrogation channel and said second infrared spectral band provides a reference channel.

11. The method for generating multi-spectral image data for a cytological specimen as claimed in claim 9, wherein said spectral bands comprise a first optical band centered at 530 nanometers, a second optical band centered at 630 nanometers, and a third optical band centered at 577 nanometers, and said infrared spectral band comprises a 1215 $cm^{-1}$ band.

12. The method for generating multi-spectral image data for a cytological specimen as claimed in claim 10, wherein said first infrared spectral band comprises a 1215 $cm^{-1}$ band and said second infrared spectral band comprises a 1240 $cm^{-1}$ band.

* * * * *